US009621684B2

(12) United States Patent
Oleson et al.

(10) Patent No.: US 9,621,684 B2
(45) Date of Patent: Apr. 11, 2017

(54) METHOD AND ARRANGEMENT FOR MONITORING PHYSIOLOGICAL DATA

(71) Applicant: Under Armour Inc., Baltimore, MD (US)

(72) Inventors: Mark A. Oleson, Baltimore, MD (US); F. Grant Kovach, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 333 days.

(21) Appl. No.: 14/175,457

(22) Filed: Feb. 7, 2014

(65) Prior Publication Data

US 2014/0222943 A1 Aug. 7, 2014

Related U.S. Application Data

(60) Provisional application No. 61/762,175, filed on Feb. 7, 2013.

(51) Int. Cl.
| | |
|---|---|
| *G06F 15/173* | (2006.01) |
| *H04L 29/06* | (2006.01) |
| *A61B 5/00* | (2006.01) |
| *G06F 19/00* | (2011.01) |
| *H04L 29/08* | (2006.01) |

(52) U.S. Cl.
CPC ............ *H04L 69/16* (2013.01); *A61B 5/7214* (2013.01); *G06F 19/3481* (2013.01); *H04L 67/12* (2013.01)

(58) Field of Classification Search
CPC ........ A41D 15/005; A41D 13/08; A41D 1/00; A61B 2503/10; A61B 5/0002; A43B 5/00; A41C 3/0057; A41C 3/08; G06K 9/00342; H04W 4/02; H04L 51/04; H04L 12/581; H04L 51/32; H04L 51/24
See application file for complete search history.

(56) References Cited

U.S. PATENT DOCUMENTS

| | | | | |
|---|---|---|---|---|
| 5,454,376 | A * | 10/1995 | Stephens | A61B 5/6805 600/534 |
| 6,755,795 | B2 * | 6/2004 | Marmaropoulos | A61B 5/02055 128/897 |
| 7,173,437 | B2 * | 2/2007 | Hervieux | A41D 13/1281 324/663 |

(Continued)

*Primary Examiner* — Aftab N. Khan
*Assistant Examiner* — Anh Nguyen
(74) *Attorney, Agent, or Firm* — Maginot, Moore & Beck LLP

(57) ABSTRACT

A physiological monitoring arrangement comprises a biometric sensor device coupled to a first garment, a first handheld computing device, and a second handheld computing device. The first handheld computing device is configured to act as a master in a device network and the biometric sensor is configured to act as a slave in the device network. The second handheld computing device is configured for wireless communication with both the biometric sensor device and the first handheld computing device according to the communications protocol in the device network. In particular, the second handheld computing device is configured to act as a slave to the first handheld computing device if the first handheld computing device is present in the device network, and the second handheld computing device is configured to act as a master to the biometric sensor device if the first handheld computing device is not present in the device network.

13 Claims, 10 Drawing Sheets

(56) References Cited

U.S. PATENT DOCUMENTS

| | | | |
|---|---|---|---|
| 2006/0136173 A1* | 6/2006 | Case, Jr. | A63B 24/00 702/182 |
| 2006/0200204 A1* | 9/2006 | Daum | A61N 1/365 607/19 |
| 2008/0287062 A1* | 11/2008 | Claus | H04W 12/02 455/41.2 |
| 2010/0185398 A1 | 7/2010 | Berns et al. | |
| 2011/0125866 A1* | 5/2011 | Williams | G06F 19/3418 709/217 |
| 2012/0320736 A1* | 12/2012 | Hillier | H04M 3/2263 370/218 |
| 2013/0298208 A1* | 11/2013 | Ayed | G06F 21/00 726/6 |

\* cited by examiner

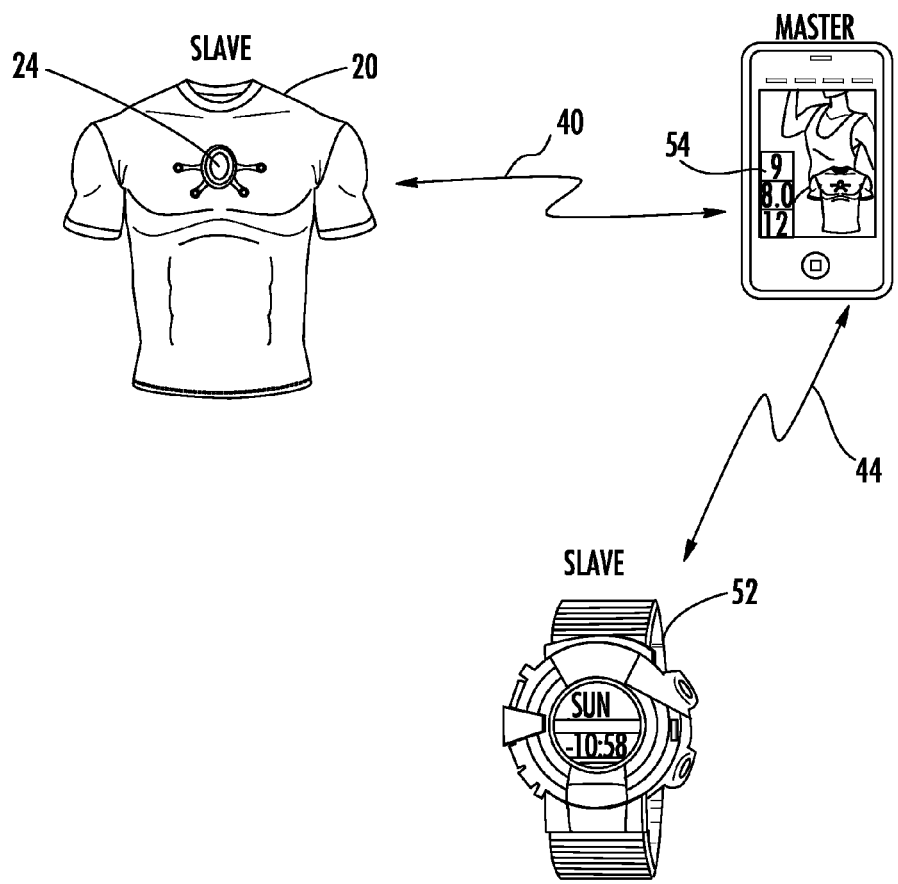
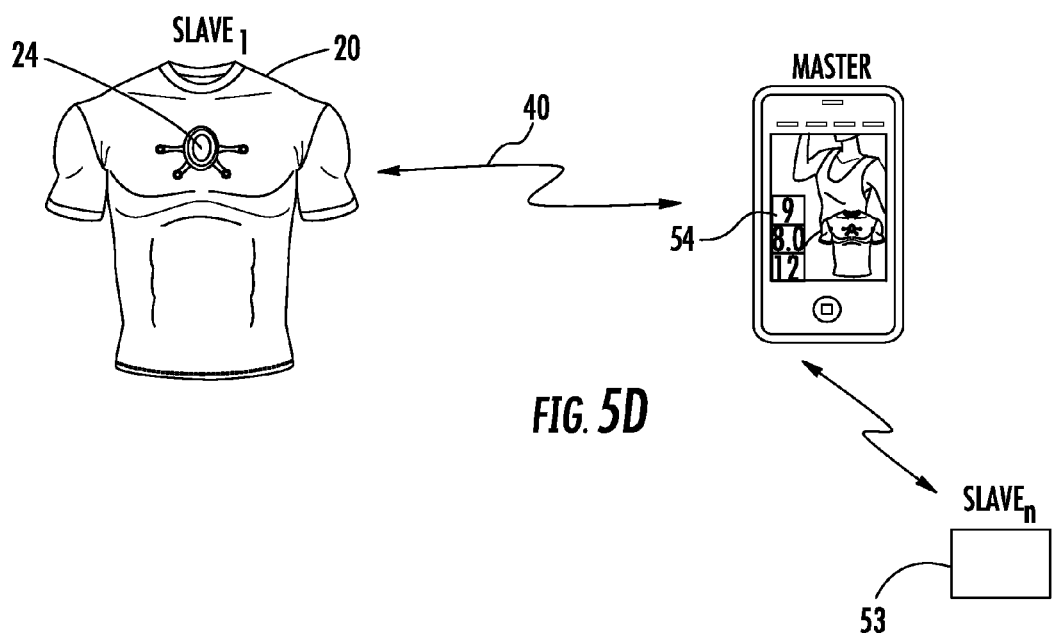
FIG. 5C
FIG. 5D

METHOD AND ARRANGEMENT FOR MONITORING PHYSIOLOGICAL DATA

CROSS-REFERENCE TO RELATED APPLICATIONS

This application claims priority from U.S. provisional patent application Ser. No. 61/762,175, filed Feb. 7, 2013, the content of which is incorporated herein by reference in its entirety.

FIELD

This application generally relates to physiological data and athletic performance monitoring, and more particularly to systems for sensing, processing and displaying biometric data.

BACKGROUND

Athletes and their trainers often keep track of the progress and conditioning of the athlete. Many computerized systems exist which collect biometric data from an athlete during training and subsequently process and display such information for use by the athlete or the trainer. Recently, such systems have become available where the sensor designed to collect the biometric data is incorporated into an athletic garment worn by the athlete. An example of such a system is disclosed in U.S. Patent Publication No. 2010/0185398.

With many existing athletic monitoring systems, biometric data for an athlete is collected by a sensing device during a training session. The biometric data collected during the training session is stored in the memory of a computer that is carried by the athlete or within a short range of the athlete. For example, an athlete may wear a heart rate monitor during a training session, and data from the heart rate monitor may be transmitted to the memory of a handheld personal computer carried by the athlete (e.g., a wristwatch, smartphone or other handheld personal computer in wired or wireless communication with the sensor). Biometric data collected by heart rate monitor or other sensing device is often transmitted to the associated handheld personal computer in real time using a short range wireless technology such as Bluetooth®. The handheld personal computer may process the data locally or may transmit data to a remote location for processing and/or storage. For example, data transmitted to the handheld personal computer may be transmitted over the cellular telephone network to an internet server or other network computer for further processing (e.g., processing within "the cloud").

In view of the foregoing, it would be advantageous to provide an accurate and reliable system and method for properly collecting biometric data from an athlete during a training session or other sporting event. It would be particularly advantageous if the system included a reliable method for insuring that collected data is not lost when communications between the sensor device and a handheld personal computer is interrupted. It would also be advantageous for the sensor device to be configured for operation in associate with any of various handheld personal devices or other computing devices that may be selected by an athlete or other user.

SUMMARY

In at least one embodiment, a physiological monitoring arrangement comprises a biometric sensor device coupled to a first garment, a first handheld computing device, and a second handheld computing device. The biometric sensor device includes a transmitter configured to transmit physiological data. The first handheld computing device is configured for wireless communication with the biometric sensor device according to a communications protocol in a device network. The first handheld computing device is further configured to act as a master in the device network and the biometric sensor is configured to act as a slave in the device network. Accordingly, the first handheld computing device is configured to receive the transmitted physiological data and display the physiological data on a first user interface. The second handheld computing device is configured for wireless communication with both the biometric sensor device and the first handheld computing device according to the communications protocol in the device network. In particular, the second handheld computing device is configured to act as a slave to the first handheld computing device if the first handheld computing device is present in the device network, and the second handheld computing device is configured to act as a master to the biometric sensor device if the first handheld computing device is not present in the device network. The second handheld computing device is configured to display the physiological data on a second user interface.

In at least one additional embodiment, a method of monitoring an individual wearing a garment with a biometric sensor is provided. The method includes obtaining physiological data from a biometric sensor device coupled to a first garment and transmitting the physiological data from the biometric sensor device. In addition, the method includes receiving the physiological data transmitted from the biometric sensor device at a first handheld computing device. The first handheld computing device is configured for wireless communication with the biometric sensor device according to a communications protocol in a device network. The first handheld computing device is configured to act as a master in the device network and the biometric sensor is configured to act as a slave in the device network. The first handheld computing device is configured to display the physiological data on a first user interface. The method further includes configuring a second handheld computing device for wireless communication with both the biometric sensor device and the first handheld computing device according to the communications protocol in the device network. The second handheld computing device is configured to act as a slave to the first handheld computing device if the first handheld computing device is present in the device network, and the second handheld computing device is configured to act as a master to the biometric sensor device if the first handheld computing device is not present in the device network.

BRIEF DESCRIPTION OF THE DRAWINGS

FIG. 5C is a diagrammatic view of a sensor module as a slave and a watch as a slave in communications with a smartphone as a master according to at least one alternative embodiment of the communications network of FIG. 3; and FIG. 5D is a diagrammatic view of a sensor module as a slave and an additional device as a slave in communications with a smartphone as a master according to at least one alternative embodiment of the communications network of FIG. 3.

DESCRIPTION

Figure 1:
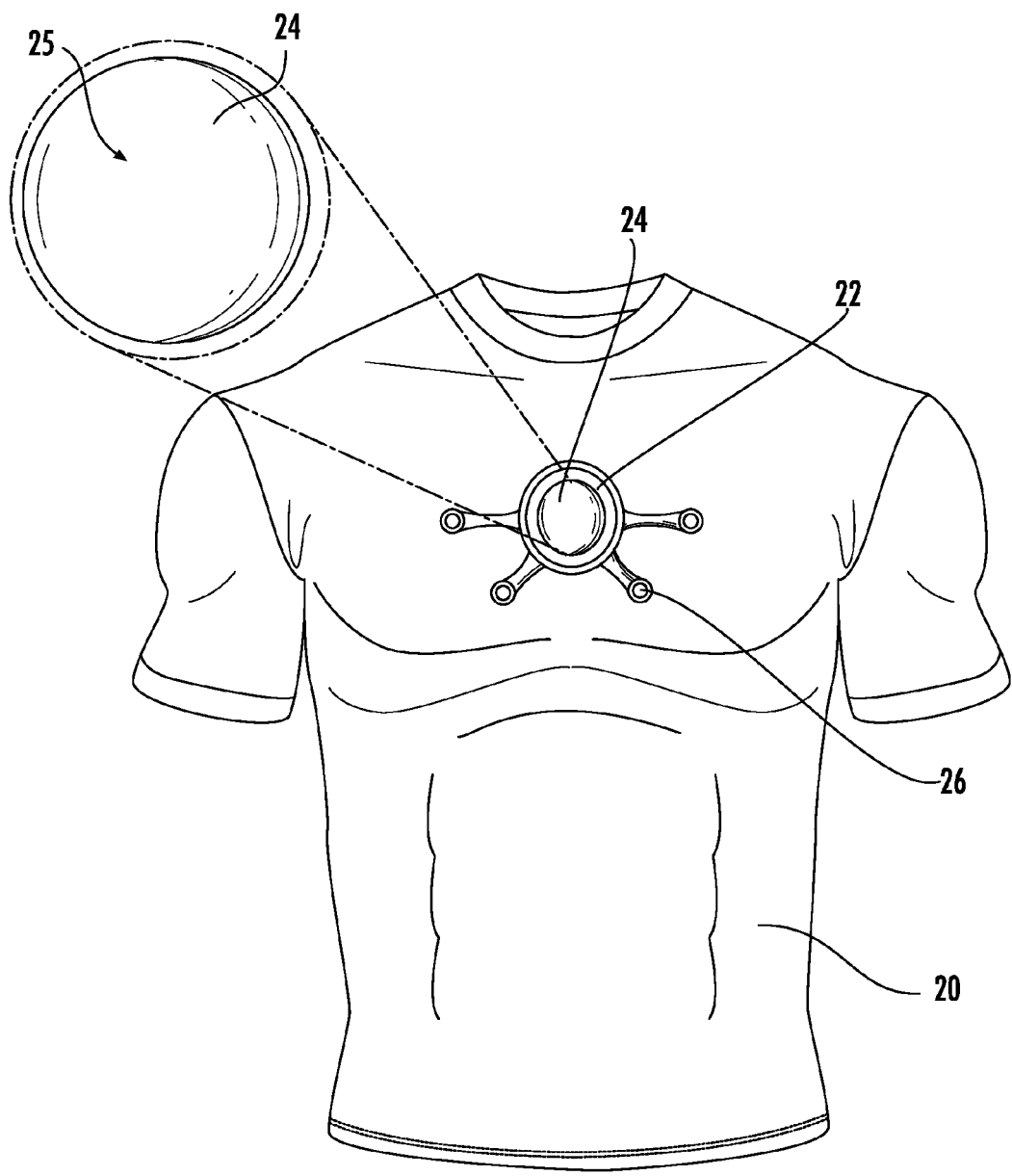
FIG. 1 is a front view of an athletic garment with a sensor module configured for use in association with a system for monitoring athletic performance.

Referring to FIG. 1, there is shown a diagrammatic view of an exemplary embodiment of a system for monitoring an athlete's performance as the athlete participates in a sporting event. The reader should understand that the embodiment discussed herein may be implemented in many alternate forms and variations. Furthermore, the word "sporting event" as used herein refers to any organized or unorganized event where a human participates in a team or individual competition, or a team or individual training session or activity. Examples of "sporting events" include both professional and amateur sports competitions (whether team or individual), team or individual practice sessions to further develop physical skills or prepare for a competition, and/or any team or individual physical workout, physical exercise, athletic conditioning or training session (whether or not in preparation for a competition), or entertainment activity involving physical exertion. The word "sporting venue" as used herein refers to a building, field, street, course, trail, stadium, facility, or any other location where a sporting event occurs. The word "athlete" as used herein refers to any human participating in a sporting event. The word "garment" as used herein refers to shirts, shorts, pants, socks, shoes, watches, wristbands, chest bands, arm bands, head bands, hats, headgear (e.g., glasses), or any other clothing, footwear, accessory or equipment worn on the human body. Furthermore, the term "handheld computing device" as used herein refers to any of various computing devices that are relatively small and portable, including smartphones, wrist watches, tablet computers, laptop computers, and other computerized personal assistant devices.

With reference now to FIG. 1, a garment 20 is shown configured to be worn on a torso portion of a human body. In particular, the garment 20 is shown in the form of a shirt. The shirt includes a receptacle 22 configured to hold a sensor device/module 24. At least one sensor 26 is positioned on the shirt or on the athlete wearing the shirt. The sensor 26 is configured to sense biometric data from the athlete wearing the shirt and deliver the sensed biometric data to a transceiver in the sensor module 24. The transceiver 29 is configured to deliver the sensed biometric data to a handheld computing device 50 (see FIG. 2) in communications with the sensor module 24.

With continued reference to FIG. 1, The receptacle 22 on the shirt may be provided in any of numerous forms, including the embodiments described in U.S. Patent Publication No. 2010/0185398 filed Jan. 22, 2010, and U.S. Patent Publication No. 2013/0077263 filed Sep. 27, 2012, the contents of which are incorporated herein in their entirety. The receptacle 22 is configured to secure the sensor module 24 in place on the garment 20 when it is worn by the user. In at least one embodiment, the receptacle 22 secures the sensor module 24 to the garment 20 in a releasable fashion such that the sensor module 24 may be removed from the garment by the user without damaging the receptacle or the garment. However, in another alternative embodiment, the sensor module 24 may be secured on the garment 20 in a permanent fashion.

Figure 2:
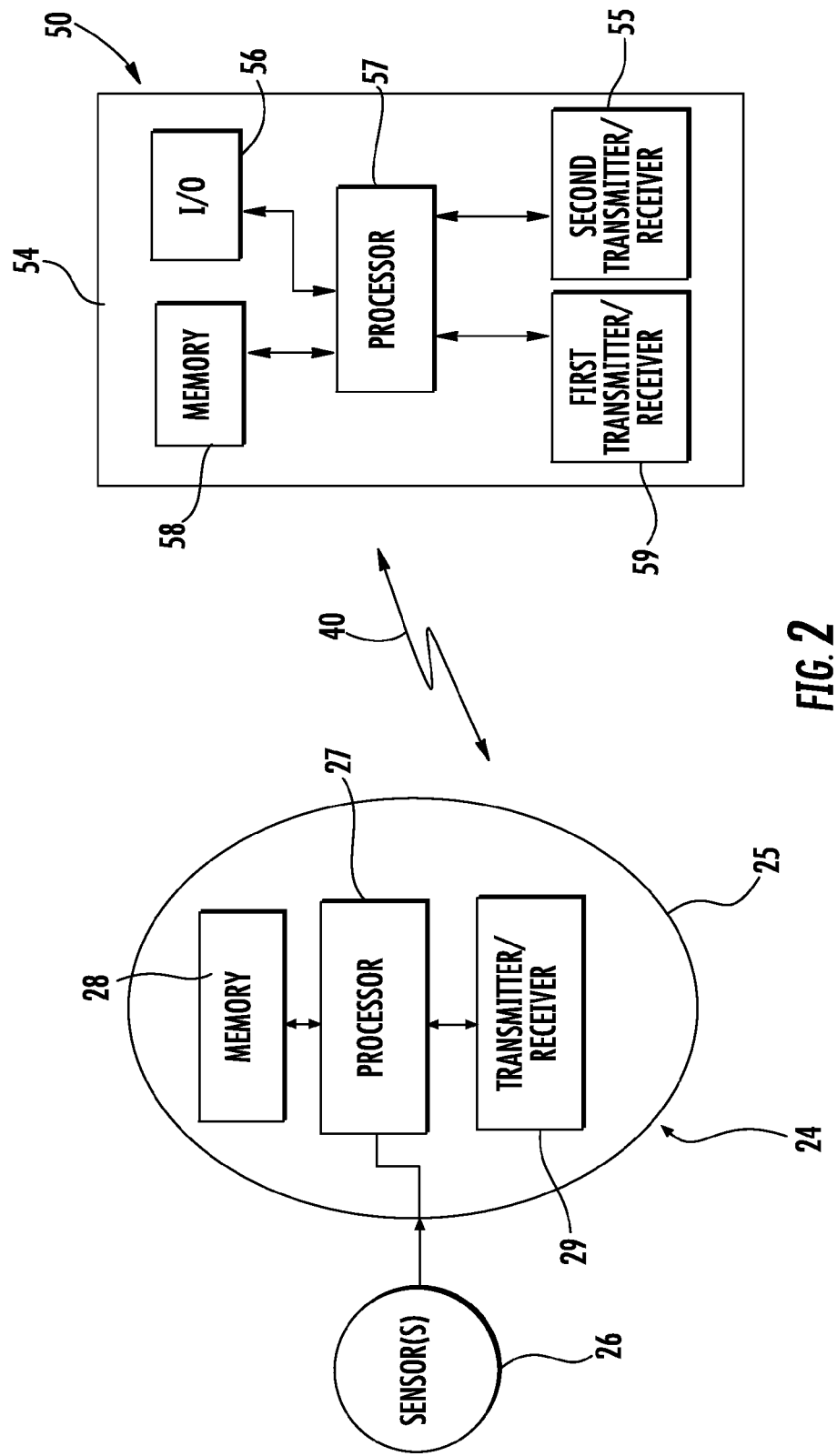
FIG. 2 is a block diagram of electronic components in the sensor module of FIG. 2 and a smartphone in communications with the sensor module.

As shown in FIG. 2, the sensor module 24 includes electronic circuitry comprising a processor 27, a memory 28, and a transceiver 29 protected within a durable shell 25. The processor 27 may be any of various processors as will be recognized by those of ordinary skill in the art, such as processors from Intel Corporation or AMD. The processor 27 is configured to receive biometric data signals from the biometric sensors 26 provided on the garment 20 or otherwise carried by the athlete. The processor 27 is connected to both the memory 28 and the transceiver 29, and may deliver received biometric data to either the memory 28 or the transceiver 29. Additionally, the processor 27 may perform some processing on the received biometric data prior to delivery to the memory 28 or transceiver 29. For example, the processor 27 may associate the received biometric data with a particular time and/or sporting event.

The memory 28 is configured to store information, and particularly data that may be retrieved, manipulated or stored by the processor 27, along with software for execution by the processor 27. The memory 28 may be of any type capable of storing information accessible by the processor, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transceiver 29 is an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The sensor module 24 also includes a battery (not shown) configured to power the electronics devices within the sensor module 24. In at least one embodiment, the battery of the sensor module 24 is a rechargeable battery. In this embodiment, the sensor module 24 may be placed in a battery charger configured for use with the sensor module in order to recharge the battery.

The electronics for the sensor module 24, including the processor 27, the memory 28, and the transceiver 29, are housed within the shell 25 to keep the electronics within the sensor module safe. Accordingly, the shell 25 may be comprised of a polymer, or fabric material capable of absorbing impacts without damage to the electronics embedded in the shell. Electrical contacts may be provided on the sensor module 24 to allow the sensor module 24 to receive biometric data signals delivered from the sensors 26 through a wire. Alternatively the transmitter 29 may be completely enclosed in the shell material and receive the signals from the sensors 26 via a wireless connection. In view of the overall shape of the shell 25 of the sensor module 24, the terms "bug" and "puck" may also be used to refer to the sensor module 24. However, the sensor module may be any of various sizes, shapes and configurations, as will be recognized by those of ordinary skill in the art.

The sensors 26 positioned on the garment 20 include any of numerous biometric sensors that may be used to sense various physiological conditions of the athlete. For example, the biometric sensors 26 may include heart rate sensors, hydration sensors, body temperature sensors, muscle fatigue sensors and numerous other sensors which may be provided in any of various different configurations and arrangements as will be recognized by those of skill in the art. Furthermore, the sensors 26 may also include environmental/positional sensors such as a GPS receiver, accelerometer, air temperature sensor or hygrometer. This data may then be transmitted from the bug to the handheld personal computing device, as explained in further detail below, where the data is then transmitted on to a wireless telephony network. The sensors may be incorporated directly into the garment, housed within the sensor module 24, or may otherwise be worn or held by the athlete during the sporting event. For example, a heart rate sensor may be embedded in a shirt worn by the athlete or may be worn on a band encircling the athlete's chest. A GPS receiver may be provided directly in the sensor module 24, may be fastened to a shirt, or may be provided on a portable media player or telephone clipped to the athlete's waistband. Of course, these are but a few examples of sensors and configurations of sensors that may be used by the athlete in association with the bug. When the sensors are incorporated into the garment 20, they may include electrical connections that lead directly to the receptacle, allowing the sensor module 24 plugged into the receptacle to receive signals from the sensors 26. Alternatively, the garment 20 may include an electrical connector adapted for connection to other sensors that are not incorporated into the garment. In yet another embodiment, the sensors may each include an associated transmitter that transmits the sensor signal to the sensor module 24 in a wireless manner.

With continued reference to FIG. 2, in at least one embodiment, the handheld computing device 50 is a smartphone 54. The smartphone 54 includes an input/output interface 56, a processor 57, a memory 58, a first transceiver 59 and a second transceiver 55. While a smartphone 54 has been shown as the handheld computing device 50 in FIG. 2, it will be appreciated that the handheld computing device 50 may be provided in other forms in addition to or in lieu of the smartphone 54. For example, the handheld computing device 50 may be provided in the form of a watch, tablet computer, or any of various other computing devices. As will be recognized by those of ordinary skill in the art, if the handheld computing device 50 is a watch, it may include much of the same functionality and components as the smartphone 54, but may not include all the same functionality or components.

The I/O interface 56 of the smartphone 54 includes software and hardware configured to facilitate communications with the athlete. The hardware may include a touchscreen display for visual communications and speakers for audio communications. The touchscreen display allows the user to see data presented on the screen and input data into the handheld computing device 50 via a keyboard on the touchscreen.

The processor 57 of the smartphone 54 may be any of various processors as will be recognized by those of ordinary skill in the art. The processor 57 is connected to the I/O interface 56, the memory 58, the first transceiver 59, and the second transceiver 55, and may deliver data to and receive data from each of these components.

The memory 58 is configured to store information, and particularly apps and other software for execution by the processor 57. The memory 58 may be of any type capable of storing information accessible by the processor, such as a memory card, ROM, RAM, write-capable, read-only memories, or other computer-readable medium.

The first transceiver 59 is an RF transmitter and receiver configured to transmit and receive communications signals over a short range using a wireless communications technology, such as Bluetooth®, using any of various communications protocols, such as TCP/IP. Such transceivers are well known and will be recognized by those of ordinary skill in the art. The smartphone 54 also includes a battery (not shown) configured to power the first transceiver 59 and various other the electronic components within the smartphone 54.

The second transceiver 55 is configured to allow the smartphone 54 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

Figure 3:
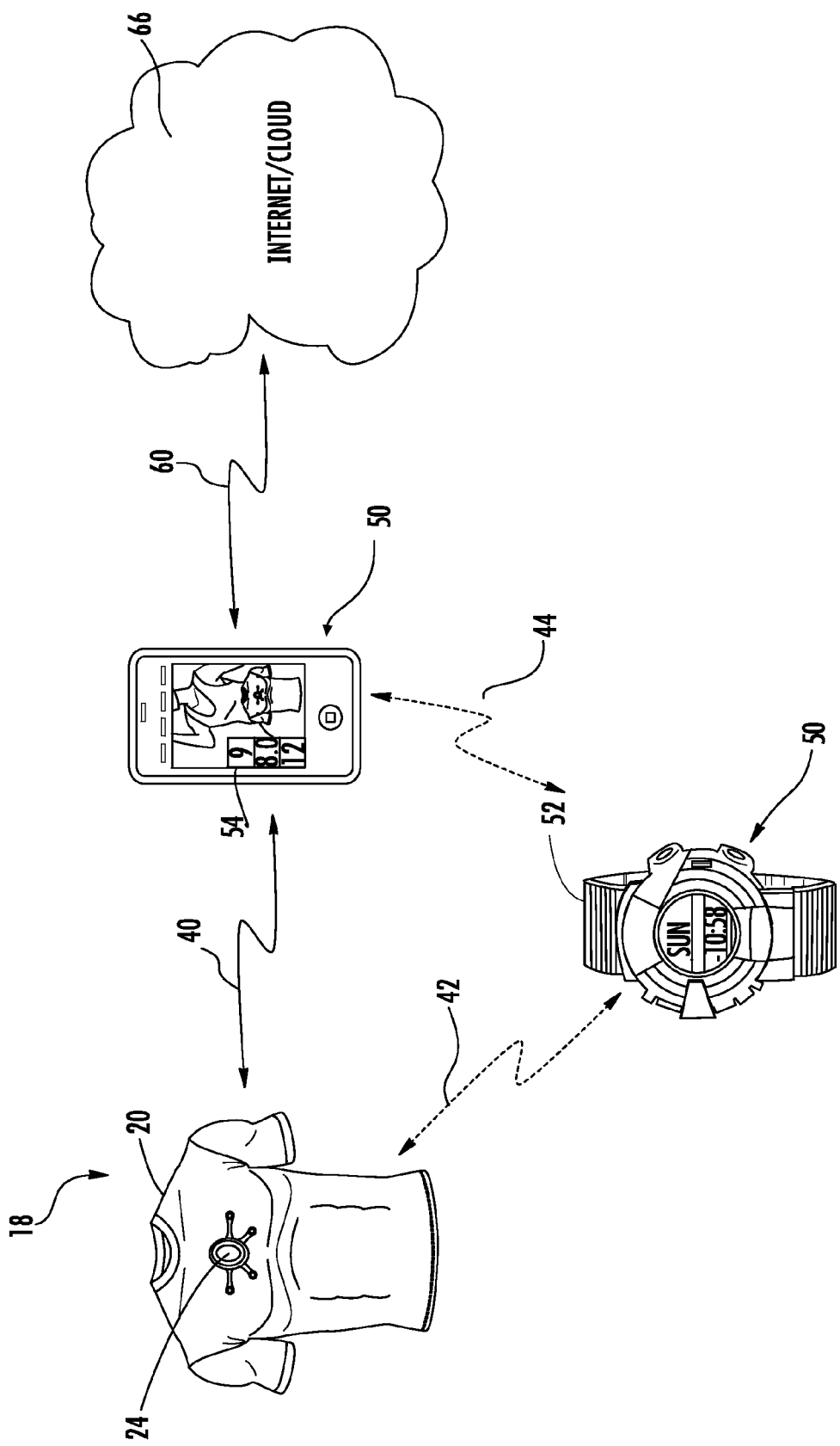
FIG. 3 is a diagrammatic view of a communications network for the system of monitoring athletic performance of FIG. 1, the communications network having a plurality of devices in wireless communication, including the sensor module, the smartphone, and a watch.

The second transceiver 55 of the smartphone 54 is configured to transmit data to the internet/cloud using a wireless telephony network, as illustrated in FIG. 3 by reference numeral 60. This wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements. The wireless telephony network, in turn, is connected to the internet/cloud 66 via the hardware of the particular mobile service provider.

Raw biometric data received by the smartphone 54 may be processed by the handheld computing device 50 or delivered to the cloud 66 for further processing. The processing to be performed may depend on various factors including the type of data received and different subscriptions of the user/athlete. Typical processing might relate to the athlete's current performance level, trends, history, training state, etc. For example, if heart rate data for the athlete is collected, the processing server may plot the data on a graph showing the athlete's heart rate during the entire sporting event. As another example, if body temperature data is collected, the processor may calculate an average body temperature during the sporting event and display the average body temperature on a historical chart of average body temperatures for other sporting events. GPS data may be used to determine various athletic data points, such as the speed of the athlete calculated over different time periods, total distance travelled, or the route taken by the athlete during a sporting event. Furthermore, the biometric data may be processed into different forms and formats, depending on the particular device that will ultimately be used to view the processed data. For example, the data may be processed into a first format that will allow it to be viewed on a watch and into a second format that will allow it to be viewed on the monitor of a personal computer. While these are but a few examples of how the raw data may be processed, those of skill in the art will recognize that nearly countless other possibilities exist for how the data received from the garment 20 will be processed for subsequent viewing and analysis.

As indicated by arrows 40, 44 and 60 in FIG. 3, after the raw biometric data is transmitted, the data is processed by the smartphone 54 or within the cloud 66. The processed data may then be displayed or otherwise presented on a user interface of one of several viewing devices, such as the smartphone 54 or the watch 52. Such devices may include screens for viewing the processed biometric data, speakers or other audible output devices for sounding information about the processed biometric data, vibration devices and/or other output devices for transmitting information related to the processed data.

In operation, when an athlete wearing the garment 20 participates in a sporting event, biometric data is delivered to the sensor module 24 from the sensors 26 worn by the athlete. As represented by arrows 40 and 42, and 44 in FIG. 3, the sensor module 24 is configured to transmit an RF signal representative of the biometric data received by the sensor module to at least one handheld computing device 50, such as the smartphone 54. In addition, the biometric data may also be transmitted to additional handheld computing devices, such as the watch 52, where the data may be conveniently displayed for the user during a sporting event. This transmission from the sensor module 24 to the handheld computing device occurs automatically without the athlete needing to prompt the transmission. Because the transmissions are automatic, some mechanism may be used to turn on the transmitter 29 of the sensor module 24 or otherwise indicate that automatic transmissions should begin. For example, in one embodiment, an on/off switch is provided on the sensor module 24 that allows the athlete to begin automatic transmissions of data from the sensor module 24. In another embodiment, the sensor module 24 may be configured to begin transmissions once it starts receiving biometric data signals from a sensor worn by the athlete. In yet another embodiment, the sensor module 24 may only begin transmissions once the data signals received from the sensor indicate that an athletic event has started (e.g., increased heart rate or temperature). In yet another embodiment, the sensor module may only begin transmissions once a confirmation signal has been received from the handheld computing device.

In addition to automatic transmissions from the sensor module 24, it will also be noted that the transmission of data from the sensor module 24 to the handheld personal computer 50 typically occur in real-time, i.e., at the same time the athlete participates in the sporting event. In one embodiment, the sensor module 24 transmits biometric data immediately upon receipt of a signal from the sensor worn by the athlete. However, in other embodiments, the sensor module 24 may be configured to conserve power by only transmitting data in a periodic fashion, such as once every second, once every ten seconds, once every thirty seconds, etc. In these embodiments, the memory 28 in the sensor module 24 may be configured to store a limited amount of data taken over a short period of time and then transmit that data and associated time period information in a single transmission. The smartphone 54, in turn, is configured to regularly and automatically transmit data to a wireless telephony network as the athlete participates in the sporting event.

User Feedback Based on Processed Heart Rate Data from Sensor

In at least one embodiment, the handheld computing device 50 (e.g., smartphone 54) is configured to determine the accuracy of heart rate information collected and assist the user in making the collected heart rate information more accurate. Heart rate data is collected from a sensor on the sensor module 24, may be filtered using a standard bandpass filter, and is then delivered to the handheld computing device 50 for processing. The heart rate data may include (i) unfiltered beat-to-beat information, including the time between heart beats and the heart rate variability (i.e., the variation in the beat-to-beat interval), and (ii) filtered heart rate data (such as the filtered measurement of beats per minute), as well as other information (e.g., ECG, etc.). In at least one embodiment, the beat-to-beat data is extrapolated over some time period (e.g., a minute), and a determination is made concerning the amount of noise in the data. The amount of noise present in the heart rate information may be determined in various ways such as an analysis of the signal-to-noise ratio in the unfiltered beat-to-beat information. As another example, noise present in the heart rate information may be determined based on a combination of the unfiltered beat-to-beat information, as well as the filtered heart rate data. For example, if the unfiltered beat-to-beat information is not consistent with the filtered heart rate data, or within a predetermined tolerance, it can be determined that an unacceptable amount of noise is present in collection of the heart rate data, and thus the heart rate data collected during the sporting event may be inaccurate. As yet another example, the noise in the heart rate information may be determined by analyzing the heart rate variability collected from the unfiltered beat to beat information and, if the time between beats varies widely, a determination may be made that inaccurate heart rate data is being collected.

When the system detects that the collected heart rate data is inaccurate, the system urges the user to take steps to make the heart rate data more accurate. Inaccurate heart rate data is often (and most likely) the result of a faulty sensor arrangement on the user's body (e.g., improper placement of the sensor on the body, or additional moisture needed on the sensor electrodes). Thus, when a determination is made that the heart rate data is inaccurate, a message is displayed on the smartphone 54 informing the user that the system is having difficulty collecting heart rate information and providing instructions for adjustment of the heart rate sensor in an attempt to obtain more accurate heart rate data. Examples of instructions provided to the user may include an instruction to "adjust your strap", "moisten the electrodes on the sensor", or showing an illustration of proper sensor placement on the body. An additional example of an instruction to the user includes asking the user to stand still for a minute, thus allowing the system to determine if the noisy heart rate signal is simply a result of a high activity level by the user or an improper sensor arrangement or improper sensor functionality. These instructions may be provided on a display screen and/or audibly with a voice message or warning tones. If appropriate actions by the user do not result in correction of the collected heart rate data, a message may be displayed or otherwise communicated instructing the user to take his or her sensor module to a service center for further analysis.

Data Transmission Based on Signal Strength

In certain circumstances, the sensor module 24 is further configured to temporarily suspend data transmissions when communications between the sensor module 24 and the handheld computing device are disrupted. In these situations, the sensor module 24 temporarily saves the data that would normally be transmitted to the handheld computing device 50 in real time to the internal memory 28 on the sensor module 24. In at least one embodiment, the internal memory 28 on the sensor module 24 is configured to retain ten hours or more of biometric data received from the sensor. However, it will be recognized that the memory 28 may be configured to retain any of various amounts of data.

Various reasons may exist for the determined signal strength to be less than a threshold value. For example, the distance between the sensor module 24 and the smartphone 54 may be too great for a proper signal to be received at the smartphone 54, such as when an athlete participates in a sporting event carrying the sensor module 24 but not carrying the smartphone 54. As another example, battery power in either the sensor module 24 or the smartphone 54 may be low, resulting in a weak signal transmission.

In at least one embodiment, the processor 27 of the sensor module 24 determines that communications have been disrupted when a signal strength for communications with the smartphone 54 do not meet a certain threshold. When the sensor module 24 suspends transmission of data to the smartphone 54, the sensor module saves the data in internal memory 28. This data is saved in the internal memory 28 until a later time when an acceptable signal strength is achieved between the sensor module 24 and the smartphone 54. "Signal strength" generally refers to a received signal level or field strength. It is often expressed in dB-microvolts per metre (dBμV/m) or in decibels above a reference level of one milliwatt (dBm). Various metrics have been established to provide an indication of signal strength. For example, Bluetooth® uses the received signal strength indicator (RSSI) measurement to provide a measurement of the power level of an RF signal received by an antenna. Thus, in the embodiment disclosed herein, the transmitter/receiver 29 provides an RSSI number to the processor 27 to provide an indication of the signal strength between the sensor module 24 and the smartphone 54. The higher the RSSI number (or less negative in some embodiments), the stronger the signal.

Figure 4:
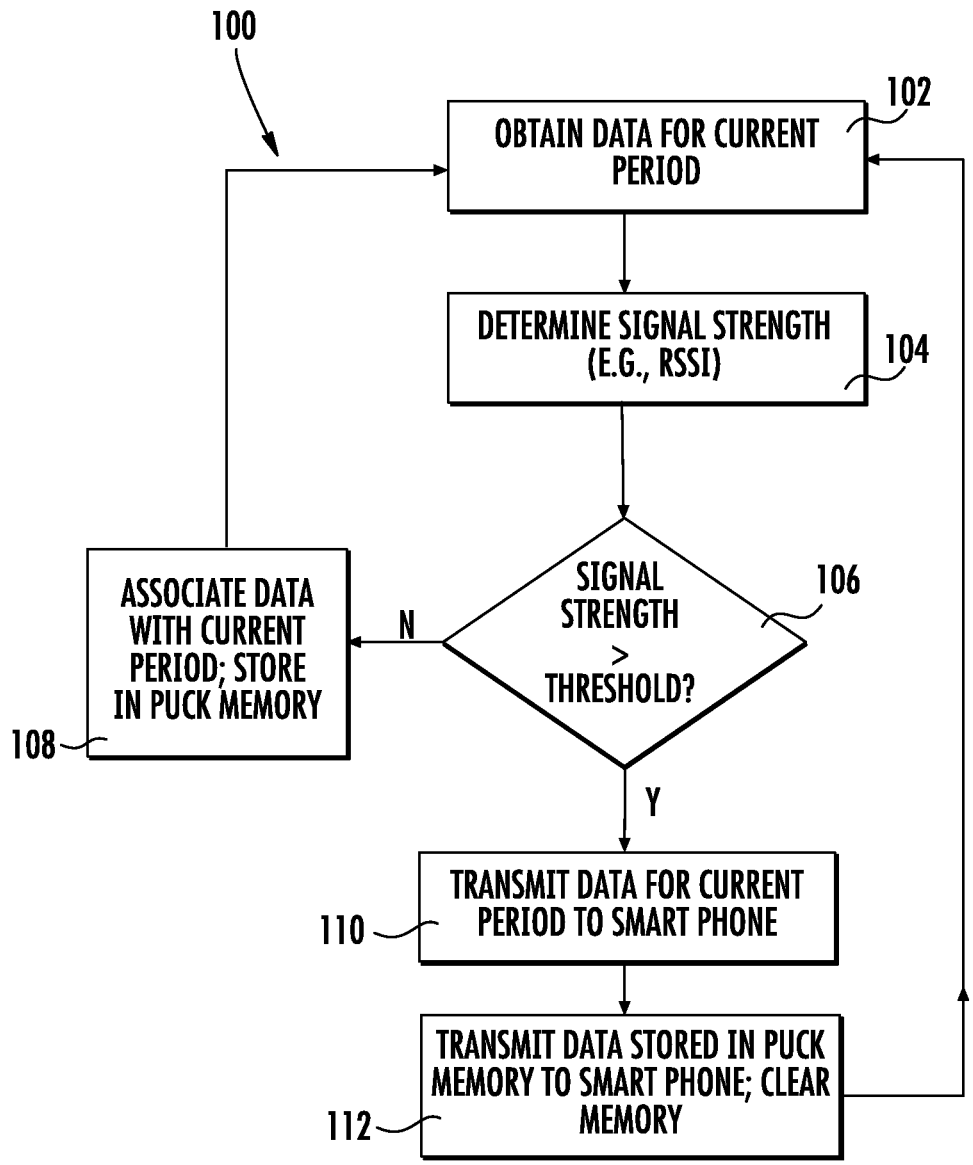
FIG. 4 is a flowchart of a method of storing and transmitting data using the communications network of FIG. 3.

With reference now to FIG. 4, a method 100 is disclosed for managing data transmissions from the sensor module 24 to the smartphone 54. The method begins in block 102 when the processor 27 obtains data for a current time period from the sensors 26. As discussed above, the data may be any of various types of biometric data such as heart rate data, accelerometry data, or temperature. Accordingly, examples of collected data may be a heart rate measured in beats per second, an angle of inclination, or body temperature. The time period may be any of various intervals of time, such as one second, five seconds, thirty seconds, or any other period of time deemed appropriate for the collection of the desired biometric data.

In block 104 the processor 27 determines a current signal strength for a signal received from the sensor module 24. The determination of signal strength may be according to one of various known metrics, such as RSSI. In general, RSSI may be used to determine an amount of radio energy in a channel. The processor 27 in the sensor module 24 observes an RSSI value indicative of a measured signal strength provided from the communications card of the transceiver 29 or other wireless network monitoring tool. Different wireless network monitoring tools will provide different RSSI values. For example, one communications card may provide RSSI values between 0 to 100, while another communications card may provide RSSI values between 0 to 127. Because there is no standardized relationship of any particular physical parameter to the RSSI reading, different card vendors provide their own accuracy, granularity, and range for the actual power (typically measured as mW or dBm) and their range of RSSI values (e.g., from 0 to RSSI_Max).

A threshold value is pre-determined as an acceptable for data transmission between the sensor module 24 and the smartphone 54. This threshold value will generally depend on the range of RSSI values associated with the transceiver 29, as described above. Accordingly, in block 106, the processor determines whether the signal strength determined in block 104 is greater than the threshold value.

If the determined signal strength is less than the threshold value in block 106, communications between the sensor module 24 and the smartphone 54 have been disrupted or are not at an acceptable level, and the method proceeds to block 108. In block 108, the recently collected data for the current period is stored in memory 28 on the sensor module 24. The stored data is associated with the current time period within the memory 28. Thus, when the data is recalled from memory 28, the time period when the data collected may also be retrieved.

If the determined signal strength is greater than the threshold value in block 106, communications between the sensor module 24 and the smartphone 54 are at an acceptable level, and the method proceeds to block 110. In block 110, the processor delivers the recently collected data to the transmitter 29, and the data is transmitted to the smartphone 54 for further processing.

After transmission of the data for the current time period in block 110, the method proceeds to block 112, where the processor 27 retrieves all the data stored in memory 28 for any previous time periods and delivers this data to the transmitter 29 for transmission to the smartphone 54. As mentioned above, the data transmitted from the memory 28 to the smartphone 54 includes time period information associated with the collected biometric data. Thus, when this data is received by the smartphone 54, the smartphone is provided with sufficient information to reconstruct the sequence of biometric data provided by the sensors 26 during the entire time communications with the sensor module 24 were disrupted. After transmission of this data from the memory 28, the processor clears the memory, wiping the memory clean of all data already transmitted to the smartphone 54.

Master/Slave Communications Arrangement

As described above, and as shown in FIG. 3, devices in an athletic performance monitoring network 18 (which may also be referred to herein as a "device network") include the sensor module 24, the watch 52, the smart phone 54, and devices connected to the smartphone 54 via the cloud 66. In at least one embodiment of the device network 18, the senor module 24 communicates with the watch 52 and the smartphone 54 using Bluetooth® technology. This technology provides a peer-to-peer closed communication arrangement for wireless communications between the sensor module 24, the watch 52, and the smartphone 54. In this communication arrangement, a single device may only communicate with one other device at a given time (e.g., the sensor module 24 can only communicate with either the watch 52 or the smartphone 54, but cannot communicate with the watch 52 and the smartphone 54 at a given time). This potentially limits the functionality of the devices during a sporting event. For example, if a user carries both the watch 52 and the smartphone 54 during an activity, only one of these devices serves as the output/display device at a given instant, as the sensor module 24 is configured to communicate with only one device at a given time. In this peer-to-peer closed communication arrangement, it is difficult for the sensor module to properly communicate with both the watch 52 and the smartphone 54. Moreover, if a biometric sensor is also included on the watch 52, and the watch is only communicating with the sensor module 24, the data from the sensor on the watch may not be available on the phone. Therefore, the sensor module, watch 52, smartphone 54, or other handheld computing devices in the arrangement disclosed herein are configured to communicate under a master-slave communication arrangement, as described below.

Different scenarios are possible for use of the devices (i.e., the sensor module 24, the watch 52, and the smartphone 54) in the device network 18. In a first scenario, a user participates in a sporting event using only the sensor module 24 and the phone 54. In a second scenario, the user participates in the sporting event using only the sensor module 24 and the watch 52. In a third scenario, the user participates in the sporting event using the sensor module 24, the watch 52 and the phone 54. In order for all three scenarios to operate effectively, an embodiment of the device network 18 may be utilized wherein the devices (e.g., 24, 52 or 54) communicate under a master/slave communication arrangement. In this master/slave arrangement, at least one of the devices is configured to selectively operate as either a master or a slave, depending on which devices are in communication with each other, as explained in further detail below.

Figure 5A:
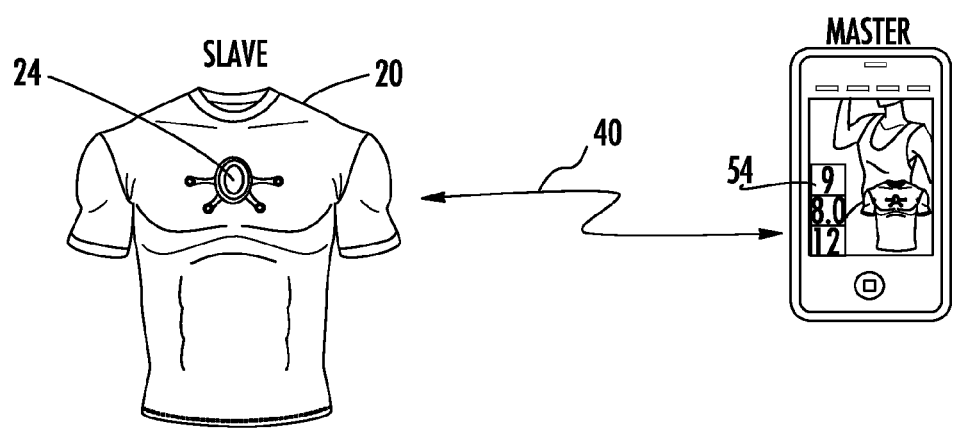
FIG. 5A is a diagrammatic view of a sensor module as a slave in communications with a smartphone as a master according to at least one alternative embodiment of the communications network of FIG. 3.

With reference now to FIG. 5A, in the first scenario under the master/slave arrangement, the sensor module 24 and the smartphone 54 are the two devices in communication during the sporting event. In this scenario, the smartphone 54 is the master and the sensor module 24 is the slave. Before communications are established between the sensor module 24 and the smartphone 54, the sensor module 24 is in an advertising mode where it sends signals to alert any other devices in the area of its presence (i.e., "advertising"). However, in the advertising mode, the sensor module 24 does not transmit any biometric data or other collected sensor data. When the smartphone 54 receives the advertising signal from the sensor module 24, communications between the sensor module 24 and the smartphone 54 are established with the sensor module 24 acting as a slave and the smartphone 54 acting as a master. Accordingly, the sensor module 24 only transmits sensor data when instructed to do so by smartphone 54. Furthermore, once communications are established between the sensor module 24 and the smartphone 54, the sensor module 24 cannot communicate with any other devices, as its communications are locked to its master (the smartphone 54).

Figure 5B:
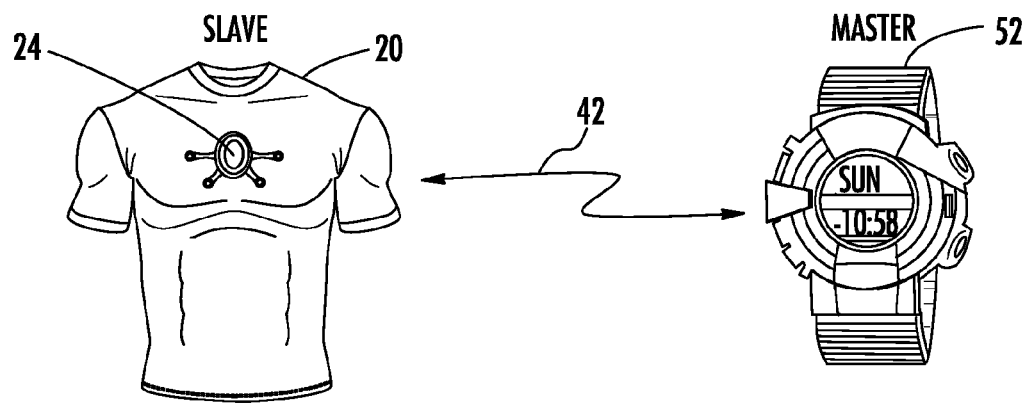
FIG. 5B is a diagrammatic view of a sensor module as a slave in communications with a watch as a master according to at least one alternative embodiment of the communications network of FIG. 3.

With reference now to FIG. 5B, in the second scenario under the master/slave arrangement, the sensor module 24 and the watch 52 are the two devices in communication during the sporting event. In this scenario, the watch 52 is the master and the sensor module 24 is the slave. Similar to the above-described sensor module/smartphone arrangement, after communications are established between the watch 52 and the sensor module 24, the sensor module 24 only transmits sensor data when instructed to do so by watch 52. Furthermore, once communications are established between the sensor module 24 and the watch 52, the sensor module 24 cannot communicate with any other devices, as its communications are locked to its master (the watch 52).

With reference now to FIG. 5C, in the third scenario under the master/slave arrangement, the sensor module 24, watch 52 and smartphone 54 are all in communication during a sporting event. In this scenario, the smartphone 54 is the master and the sensor module 24 and the watch 52 are both slaves. Similar to the above-described arrangements, after communications are established between the sensor module 24 and the smartphone 54, the sensor module 24 (a slave) only transmits sensor data when instructed to do so by smartphone 54 (the master). Additionally, after communications are established between the watch 52 and the smartphone 54, the watch 52 (a slave) only transmits sensor data when instructed to do so by smartphone 54 (the master). Once communications are established between the sensor module 24 and the smartphone 54, the sensor module 24 cannot communicate with any other devices, as its communications are locked to its master (the smartphone 54). Also, once communications are established between the watch 52 and the smartphone 54, the watch 52 is a slave and cannot communicate with any other devices, as its communications are locked to its master (the smartphone 54). The smartphone 54 may also transmit data to the watch 52 or the sensor module 24, if appropriate. For example, in the embodiment of FIG. 5C, the smartphone 54 may transmit sensor data received from the sensor module 24 on to the watch 52 for display on the watch face (i.e., the watch display).

As explained above, in the third scenario the watch 52 acts as a slave in the communications arrangement, while in the second scenario the watch 52 acts as a master in the communications arrangement. Data from the sensor module 24 is still displayed on the watch 52 in the third scenario, but sensor data travels from the sensor module 24 to the smartphone 54 and from the smartphone 54 to the watch 52 in this situation, instead of data transfer directly from the sensor module 24 to the watch 52 as shown in FIG. 5B. However, this data transfer route of FIG. 5C is completely transparent to the user, and will appear to be no different than the scenario shown in FIG. 5B, as the user has no concern for the path the sensor data takes in travelling from the sensor module 24 to the watch 52.

The foregoing scenarios provide the user with great flexibility to use any of various devices during a workout. In particular, a user may choose to participate in a sporting event with or without the smartphone 54 and with or without the watch 52. Significantly, both the watch 52 and the smartphone 54 may be used to display or otherwise deliver data to the user during the sporting event should the user choose to use both the watch 52 and the smartphone. Thus, the user is not limited to the use of a single display device or a single data output device. Moreover, because the sensor module is configured to save data, as described previously, the user may choose to participate in a sporting event with neither the watch 52 nor the smartphone 54, but the data collected by the sensor device 24 will not be lost.

The foregoing scenarios also illustrate the adaptability of the master/slave arrangement. In particular, the above-described master/slave arrangement is configured to allow additional devices to be added to the communications network. FIG. 5D illustrates this adaptability, showing that the smartphone 54 can be a master to as many slaves as are authenticated within the communications network. In particular, in FIG. 5D, the sensor module 24 is a first slave and the device 53 is the $n^{th}$ slave to the master smartphone 54.

Accordingly, the above described communications network with the master/slave arrangement facilitates the addition of additional sensor devices or I/O devices as determined by the manufacturer, such as footwear sensors, headgear sensor or display, tablet computers, or any of various other sensors or display devices.

Figure 6:
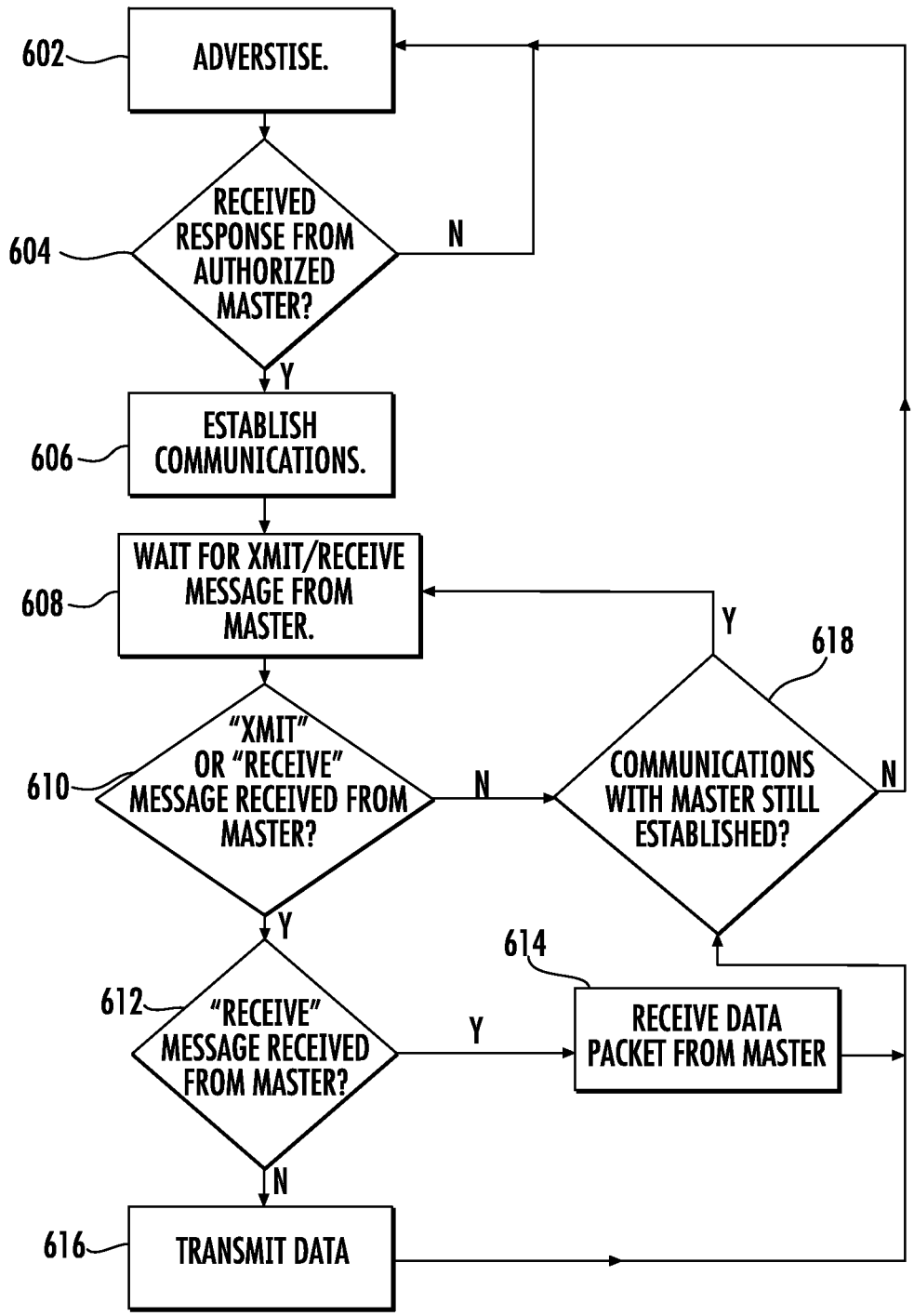
FIG. 6 is a flowchart of communications processing by a slave of the at least one alternative embodiment of the communications network of FIGS. 5A-5D.

The flowcharts of FIGS. 6-8B further illustrate communications activities of the various devices in the network in the above-described scenarios. FIG. 6 shows operation of the slaves (i.e., sensor module 24 or other slaves) when connecting to and communicating with a master. In step 602 of FIG. 6, the slave is in the advertising mode and sends out an advertising signal letting any masters (e.g., the smartphone 54 or the watch 52) in the transmission range know that the slave is available for data communications. In step 604, the slave determines whether a response to the advertise signal has been received from an authorized master. If a response from an authorized master has been received, the slave establishes communications with the master in step 606. Once communications between the slave and the master are established, the slave waits for a "transmit" or "receive" message from the master in step 608. As illustrated by this step, slave communications are dependent upon communications from the master at this point. In step 610, following the wait period of step 608, the slave determines whether a "transmit" or "receive" signal was received from the master. If no "transmit" or "receive" signal was sent, the slave determines whether communications with the master are still established in step 618. On the other hand, if a "transmit" or "receive" signal was sent, the slave processing continues in step 612 to determine whether the signal was a "receive" signal. If the signal from the master was a "receive" signal, the slave continues processing in step 614 and receives the data packet from the master. On the other hand, if the signal from the master was a "send" signal, the slave continues processing in step 616 and transmits the requested data to the master. Then, in step 618, the slave again determines if communications with the master are still established. If communications are established, the slave continues to wait for further instruction from the master in step 608. However, if communications with the master have been lost (e.g., the RSSI signal strength has fallen below the predetermined threshold) for some reason, the slave returns to the advertising mode, as shown in step 602.

Figure 7:
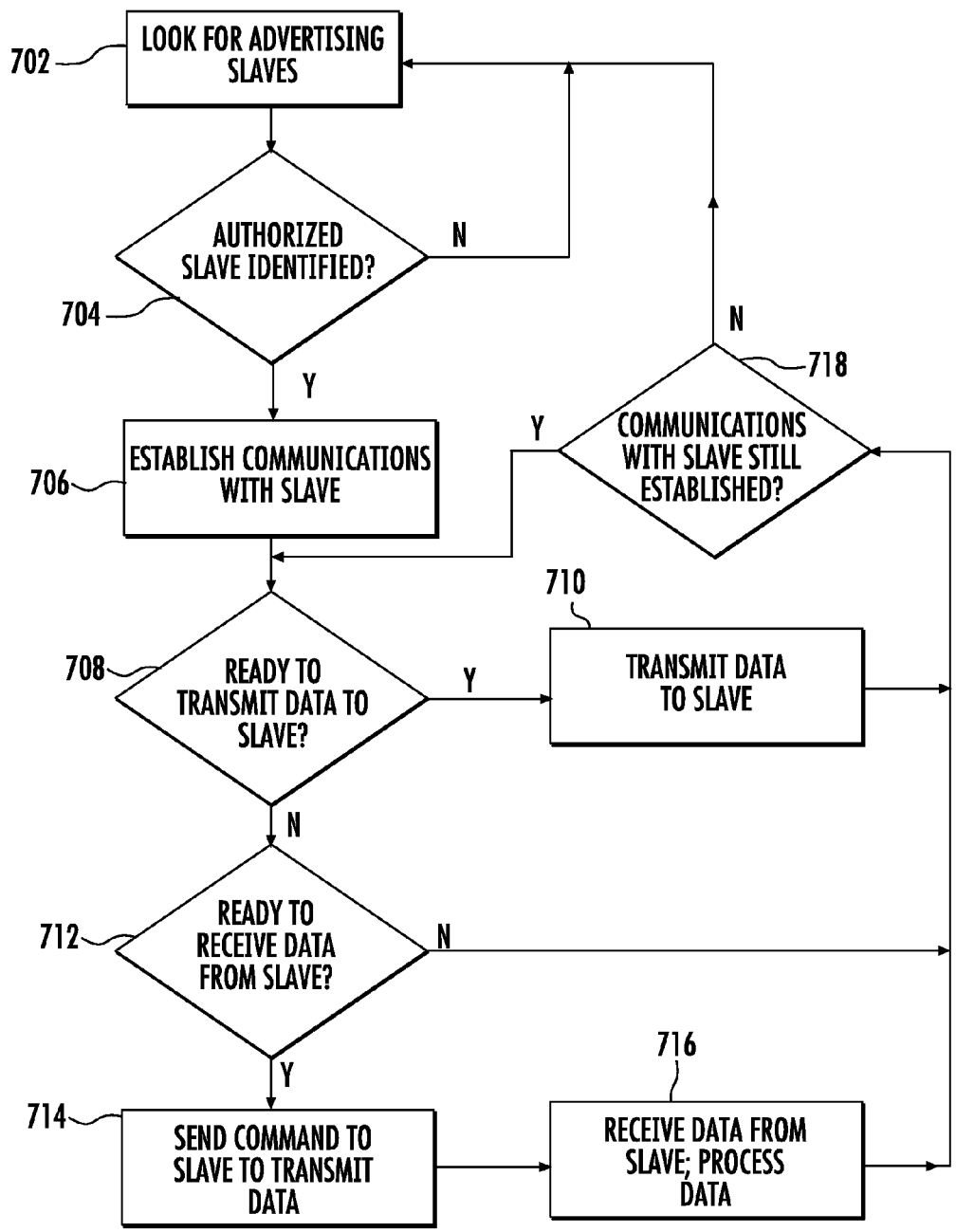
FIG. 7 is a flowchart of communications processing by a master of the at least one alternative embodiment of the communications network of FIGS. 5A-5D.

FIG. 7 shows operation of the master (i.e., the smartphone 54 or other master) when connecting to and communicating with a slave. In step 702 of FIG. 7, the master is in a search mode looking for signals advertising slaves. In step 704, the master determines whether any of the signals received from advertising slaves are authorized slaves. If an authorized slave is identified, the master established communications with the authorized slave in step 706. Next, in step 708, the master determines whether the master is ready to transmit data to the slave. If the master is ready to transmit data to the slave, the master continues processing in step 710 and transmits one or more data packets to the slave. Alternatively, if the master is not prepared to transmit data in step 708, the master continues processing in step 712 and determines whether the master is ready to receive data from the slave. If the master is ready to receive data from the slave, the master sends a command to the slave in step 714, instructing the slave to transmit data. Then, in step 716, the master receives data from the slave and processes the data. This data processing may be internal within the master or may be sent elsewhere (e.g., the cloud 66) for further processing. Then, in step 718, the master determines whether communications with the slave are still established.

If communications with the slave are still established, the master continues processing in step 708 and determines whether it is time to transmit data (or receive data in step 712). On the other hand, if communications with the slave have been disrupted, the master returns to the search mode in step 702 and continues looking for advertising slaves. In at least one alternative embodiment, step 718 is bypassed, and the master always returns to step 702 after either a data transmission or data reception. This allows the master to continually add new slaves to the communications network.

Figure 8A:
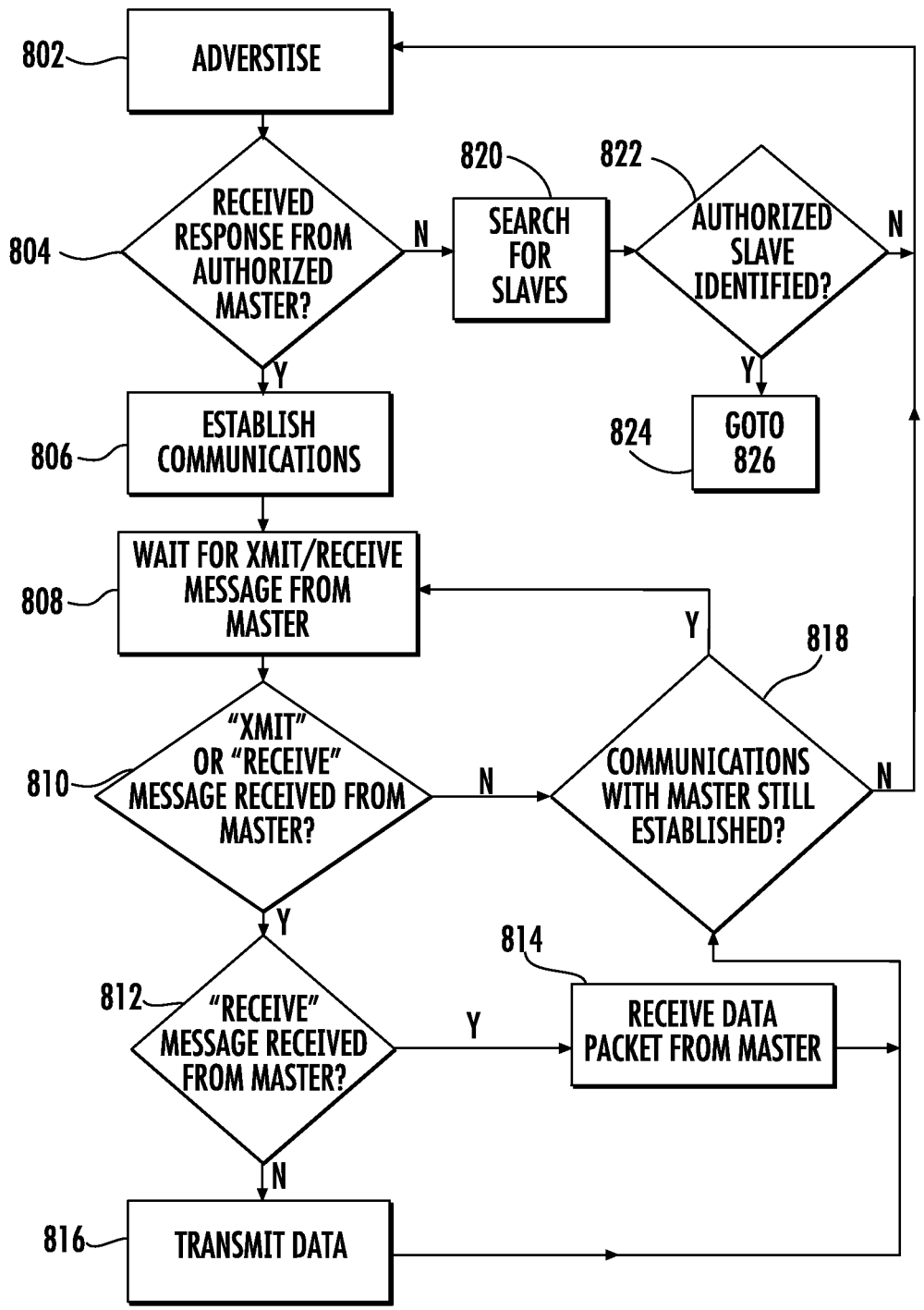
FIGS. 8A and 8B are flowcharts of communications processing by a dual role device of the at least one alternative embodiment of the communications network of FIGS. 5A-5D.
Figure 8B:
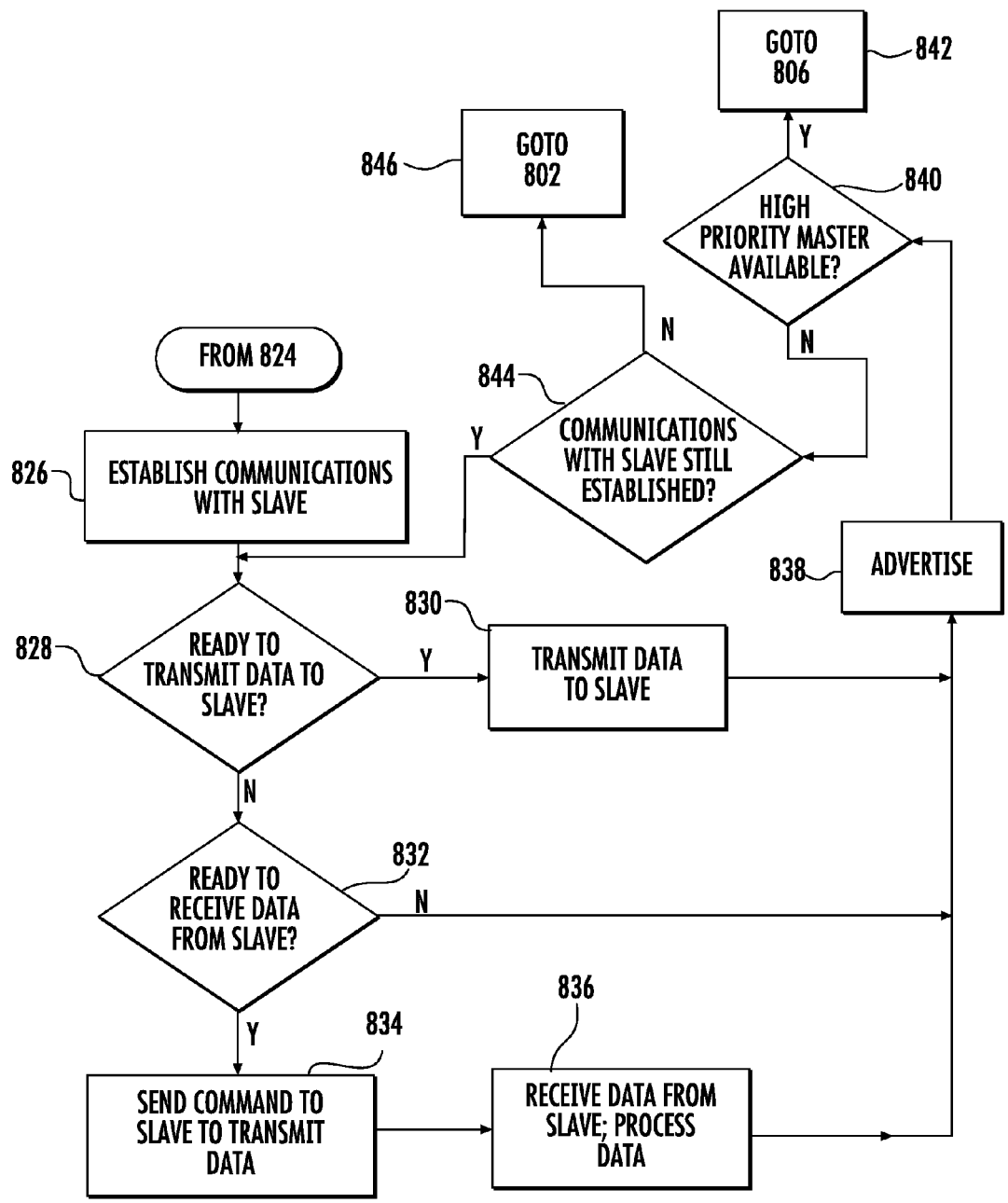

FIGS. 8A and 8B show operation of devices configured for selective operation as either a master or a slave (e.g., the watch 52 or other "dual role" devices). In step 802 of FIG. 8A, the dual role device is in an advertising mode, advertising itself as a slave for an available master in the device network. In step 804, the dual role device determines whether an authorized master is available. If a master is available, the dual role device establishes communications with the master in step 806. Steps 806 to 818 are identical to steps 606 to 618 of FIG. 6 described above. Accordingly, the discussion of these steps is not repeated herein. However, step 804 is different from step 604 in that if no authorized master is found for the dual role device, the device does not immediately continue to advertise. Instead, the dual role device searches for slaves in step 820 if no authorized master is identified in step 804. In step 822, if an authorized slave is not identified, the dual role device returns to step 802 and advertises again as a slave looking for an available master. On the other hand, as noted in steps 822 and 824, if an authorized slave is identified, the dual role device moves on to step 826 of FIG. 8B.

FIG. 8B shows operation of a dual role device when acting as a master in the device network. In particular, as noted at step 826, the dual role device establishes communications with an authorized slave in the device network. Steps 826 to 836 are identical to steps 706 to 716 of FIG. 7. Accordingly, the discussion of these steps is not repeated herein. However, the flowchart of FIG. 8B diverges from the flowchart of FIG. 7 at step 838. In step 838 of FIG. 8B, after the dual role device has either transmitted data to a slave or received data from the slave, the device checks again to determine whether it should remain a master, or whether the dual role device itself should become a slave to another master in the network. Accordingly, at step 838, the dual role device advertises itself as a possible slave in the network for an available master. In step 840 a determination is made whether a master is available. If a determination is made in step 840 that a master for the dual role device is available in the network, step 842 is implemented, and the device acts in accordance with step 806 of FIG. 8A, and communications are established between the dual role device and the available master.

It will be recognized that whether a master is available in step 840 depends on the types and configurations of the devices in the device network. Some devices in the network are configured to always act as masters of dual role devices. For example, the smartphone 54 may be configured in the network to always act as the master of a dual role device. Similarly, other devices in the network are configured to always act as slaves to dual role devices that are acting as masters. For example, the sensor device 24 may be configured in the network to always act as a slave to the dual role device, provided the dual role device is acting as a master. However, if more than one dual role device is configured for operation in the network, priorities are assigned to the dual role devices, and master or slave status between dual role devices themselves may be determined based on these priorities. For example, consider a device network wherein smart glasses and a wristwatch are both configured as a dual role devices, but the smart glasses have a higher priority than the wristwatch. Accordingly, if both the smartglasses and the wristwatch are available in the device network, and no other master is available, the smart glasses will act as a master and the wristwatch will act as a slave to the master, based on the higher priority assigned to the smart glasses than that assigned to the wristwatch.

With continued reference to FIG. 8B, if it is determined at step 840 that no master is available in the network, processing continues to step 844, and a determination is made whether communications between the dual role device and the slave are still established. If communications remain established, processing continues to steps 828 to 830, and a data is exchanged with the slave, if appropriate. However, if it is determined in step 844 that communications have been lost with the slave, the device continues to step 846 where an instruction is given to continue processing again at step 802, where the dual role device advertises itself as a slave in the network.

In view of the above, it will be recognized that three types of devices may be present in the device network. These devices include those configured to act as masters, those configured to act as slaves, and those configured to act as either a master or a slave. Dual role devices configured to act as masters or slaves will act as a master if slaves are present and no other higher priority masters are present in the device network, as explained above with reference to FIG. 8A. However, if the dual role device is acting as a master and another higher priority master presents itself in the device network, the dual role device will switch over to a slave as noted in steps 840 and 842 of FIG. 8B and step 806 of FIG. 8A.

Although the method and arrangement for monitoring physiological data has been described herein with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of any appended claims should not be limited to the description of the preferred embodiments contained herein.

What is claimed is:

1. A physiological monitoring system comprising:
    a biometric sensor device coupled to a first garment worn by a user, the biometric sensor device including a transmitter configured to transmit physiological data of the user, wherein the biometric sensor device includes a heart rate sensor and the physiological data includes heart rate data;
    a first handheld computing device configured for wireless communication with the biometric sensor device according to a communication protocol in a device network, the first handheld computing device configured to act as a master in the device network and the biometric sensor configured to act as a slave in the device network, the first handheld computing device configured to receive transmitted physiological data from the biometric sensor device and display the physiological data on a first user interface; and
    a second handheld computing device configured for wireless communication with both the biometric sensor device and the first handheld computing device according to the communications protocol in the device network, the second handheld computing device configured to act as a slave to the first handheld computing device when the first handheld computing device is present in the device network, and the second handheld computing device configured to act as a master to the biometric sensor device when the first handheld computing device is not present in the device network, the second handheld configured to display the physiological data on a second user interface,
    wherein the first handheld computing device is configured to determine whether the heart rate data is inaccurate, and if the heart rate data is determined to be inaccurate, deliver a message that the monitoring system is having difficulty collecting heart rate information and provide instructions for adjustment of the heart rate sensor; and
    wherein the second handheld computing device is configured to both (i) advertise itself as a slave in the device network for control by an available master in the device network, and (ii) search for available slaves in the device network for which the second handheld computing device will act as a master in the device network when operating in a search mode.

2. The monitoring system of claim 1 wherein the first handheld computing device is a smartphone.

3. The monitoring system of claim 1 wherein the second handheld computing device is a wristwatch.

4. The monitoring system of claim 1 wherein the garment is configured to be worn on a torso of a human body.

5. The monitoring system of claim 1 wherein the second handheld computing device is configured to establish communications with the first the first handheld computing device, the first v computing device acting as a master in the device network, the second handheld computing device configured to follow instructions from the first handheld computing device until communications with the first handheld computing device are lost, and when communications with the first handheld computing device are lost, the second handheld computing device is configured to operate in the search mode.

6. The monitoring system of claim 1 wherein the second handheld computing device is configured to establish communications with the biometric sensor device as the available slave in the device network, provide instructions to the biometric sensor device, and receive data from the biometric sensor device until an instruction is received from the available master, or if no instruction is received from the available master, until communications with the biometric sensor device are lost.

7. The monitoring system of claim 6 wherein communications with the biometric sensor device are deemed lost when a signal strength indicator falls below a predetermined threshold.

8. A method of monitoring a user wearing a garment with a biometric sensor, the method comprising:
    obtaining physiological data from a biometric sensor device coupled to a first garment of a user, wherein the biometric sensor device includes a heart rate sensor and the physiological data includes heart rate data;
    transmitting the physiological data of the user from the biometric sensor device within a device network;
    receiving the physiological data transmitted from the biometric sensor device at a first handheld computing device, the first handheld computing device configured for wireless configured for wireless communications with the biometric sensor device according to a communications protocol in the device network, the first handheld computing device configured to act as a master in the device network and the biometric sensor configured to act as a slave in the device network, the first handheld computing device configured to display the physiological data on a first user interface;

configuring a second handheld computing device for wireless communication with both the biometric sensor device and the first handheld computing device according to the communications protocol in the device network, the second handheld computing device acting as a slave to the first handheld computing device when the first handheld computing device is present in the device network, and the second handheld computing device acting as a master to the biometric sensor device when the first handheld computing device is not present in the device network;

determining whether the heart rate data is inaccurate and when the heart rate data is determined to be inaccurate delivering a message that the monitoring arrangement is having difficulty collecting heart rate information and providing instructions for adjustment of the heart rate sensor; and when operating in a search mode, operating the second handheld computing device to both (i) advertise itself as a slave in the device network for control by an available master in the device network and (ii) search for available slaves in the device network for which the second handheld computing device acting as a master in the device network.

9. The method of claim 8 wherein the first handheld computing device is a smartphone.

10. The method of claim 8 wherein the second handheld computing device is a wristwatch.

11. The method of claim 8 wherein the garment is configured to be worn on a torso of a human body.

12. The method of claim 8 further comprising, the second handheld computing device establishing communications with the first handheld computing device with wherein the first handheld computing device acting acts as a master in the device network, the second handheld computing device not operating in the search mode but following instructions from the first handheld computing device until communications with the first handheld computing device are lost, and then when communications with the first handheld computing device are lost, the second handheld computing device operating in the search mode.

13. The method of claim 8 further comprising, the second handheld computing device establishing communications with the biometric sensor device with wherein the biometric sensor device acting acts as the available slave in the device network, providing instructions to the biometric sensor device, and receiving data from the biometric sensor device until an instruction is received from the available master, or if no instruction is received from the available master, until communications with the biometric sensor device are lost.

* * * * *